United States Patent [19]
Williams

[11] Patent Number: 5,717,769
[45] Date of Patent: Feb. 10, 1998

[54] ADAPTER FOR REVERSIBLE CONVERSION OF STANDARD STETHOSCOPES TO MULTIMEDIA AND TELEMEDICINE READY STETHOSCOPES

[76] Inventor: Christopher A. Williams, 511 Oak Crest La., Wallingford, Pa. 19086

[21] Appl. No.: 387,033

[22] Filed: Feb. 10, 1995

[51] Int. Cl.⁶ ........................................... A61B 7/04
[52] U.S. Cl. ................................................. 381/67
[58] Field of Search .................. 381/67, 98; 128/715, 128/680, 773

[56] References Cited

U.S. PATENT DOCUMENTS

| | | |
|---|---|---|
| 4,362,164 | 12/1982 | Little et al. . |
| 4,528,689 | 7/1985 | Katz . |
| 4,549,551 | 10/1985 | Dyck et al. . |
| 4,679,570 | 7/1987 | Lund et al. . |
| 4,720,866 | 1/1988 | Elias et al. . |
| 4,723,555 | 2/1988 | Shue ........................................... 381/67 |
| 4,765,321 | 8/1988 | Mohri . |
| 4,770,189 | 9/1988 | Shyu . |
| 5,025,809 | 6/1991 | Johnson et al. . |
| 5,218,969 | 6/1993 | Bredesen et al. . |
| 5,348,008 | 9/1994 | Bornn et al. . |

*Primary Examiner*—Curtis Kuntz
*Assistant Examiner*—Vivian Chang
*Attorney, Agent, or Firm*—John F. A. Earley; John F. A. Earley, III

[57] ABSTRACT

Adapters and methods for reversibly converting a standard stethoscope to a multimedia and/or telemedicine ready stethoscope. The adapter includes a housing having a conduit for conducting sound therethrough, a first coupler for coupling the housing to the transducer of a standard stethoscope, a second coupler for coupling the housing to the sound conduction hose of a standard stethoscope, and a second transducer for converting an audible tone to an electronic signal.

8 Claims, 3 Drawing Sheets

ADAPTER FOR REVERSIBLE CONVERSION OF STANDARD STETHOSCOPES TO MULTIMEDIA AND TELEMEDICINE READY STETHOSCOPES

BACKGROUND OF THE INVENTION

1. Field of the Invention

The present invention relates to electronic stethoscopes, and, in particular, to adapters for reversibly converting standard stethoscopes to multimedia and/or telemedicine ready stethoscopes.

2. Description of the Related Art

As computer technology continues to revolutionize the medical field with the advent of electronic clinical charts, real-time telemedicine, and the like, there is a growing need for simple, inexpensive clinical data capture devices capable of transmitting data detected by medical instruments to an electronic medium. In particular, non-invasive auscultation with a stethoscope is one of the primary means for detection and diagnosis of a variety of medical disorders concerning the heart, lungs, gastrointestinal tract, and vascular system. A vast majority of medical professionals regularly carry and use standard stethoscopes. As a result, there is a growing need for compact, simple, and inexpensive stethoscopes compatible with electronic storage, analysis and transfer devices.

Although a variety of electronic stethoscopes have been made, such stethoscopes are relatively expensive and cumbersome. Moreover, medical professionals accustomed to using standard stethoscopes have found that many electronic stethoscopes alter the quality of the sound received, thereby making recognition of particular sounds difficult or impossible. As a result, medical professionals are reluctant to give up the use of the standard stethoscope. Therefore, there is a need for a compact, simple, and inexpensive adapter for reversibly converting a standard stethoscope to a multimedia and/or telemedicine ready stethoscope without significantly or altering the look, feel, or performance of the standard stethoscope. Further, since there are a plethora of standard stethoscopes in use, there is a need for a universal adapter capable of reversibly converting as many different types of standard stethoscopes as possible.

It is accordingly an object of this invention to overcome the disadvantages and drawbacks of the known art and to provide adapters for reversible conversion of standard stethoscopes to multimedia and telemedicine ready stethoscopes.

It is a further object of this invention to provide methods for the reversible conversion of standard stethoscopes to multimedia and telemedicine ready stethoscopes.

Further objects and advantages of this invention will become apparent from the detailed description of a preferred embodiment which follows.

SUMMARY OF THE INVENTION

The present invention is directed to an adapter for a standard stethoscope having a stethoscope transducer, a tube, and an earpiece, comprising: (a) a housing having means for conducting sound therethrough; (b) means for coupling the housing to the stethoscope; (c) a second transducer in the housing for converting an acoustic signal to an electronic signal.

The present invention is also directed to a method for reversibly converting a standard stethoscope, having a stethoscope transducer, hose, and earpiece, to a multimedia ready stethoscope, comprising the steps of: (a) removing the stethoscope transducer from the hose; (b) removably coupling a housing containing a microphone to the stethoscope transducer.

BRIEF DESCRIPTION OF THE DRAWINGS

Other objects, features, and advantages of the present invention will become more fully apparent from the following detailed description of the preferred embodiment, the appended claims, and the accompanying drawings in which:

DESCRIPTION OF THE PREFERRED EMBODIMENT(S)

The present invention relates to adapters for reversibly converting standard stethoscopes to multimedia and/or telemedicine ready stethoscopes. As used herein, "standard stethoscope" means any stethoscope, generally comprising a transducer, such as a diaphragm and/or bell, a flexible sound conduction hose, and an earpiece. "Multimedia ready stethoscope" means a stethoscope capable of transmitting an acoustic signal from a patient to an electronic storage, analysis, or transfer device. "Telemedicine ready stethoscope" means a stethoscope capable of transmitting an acoustic signal to a telephone line.

Figure 1:
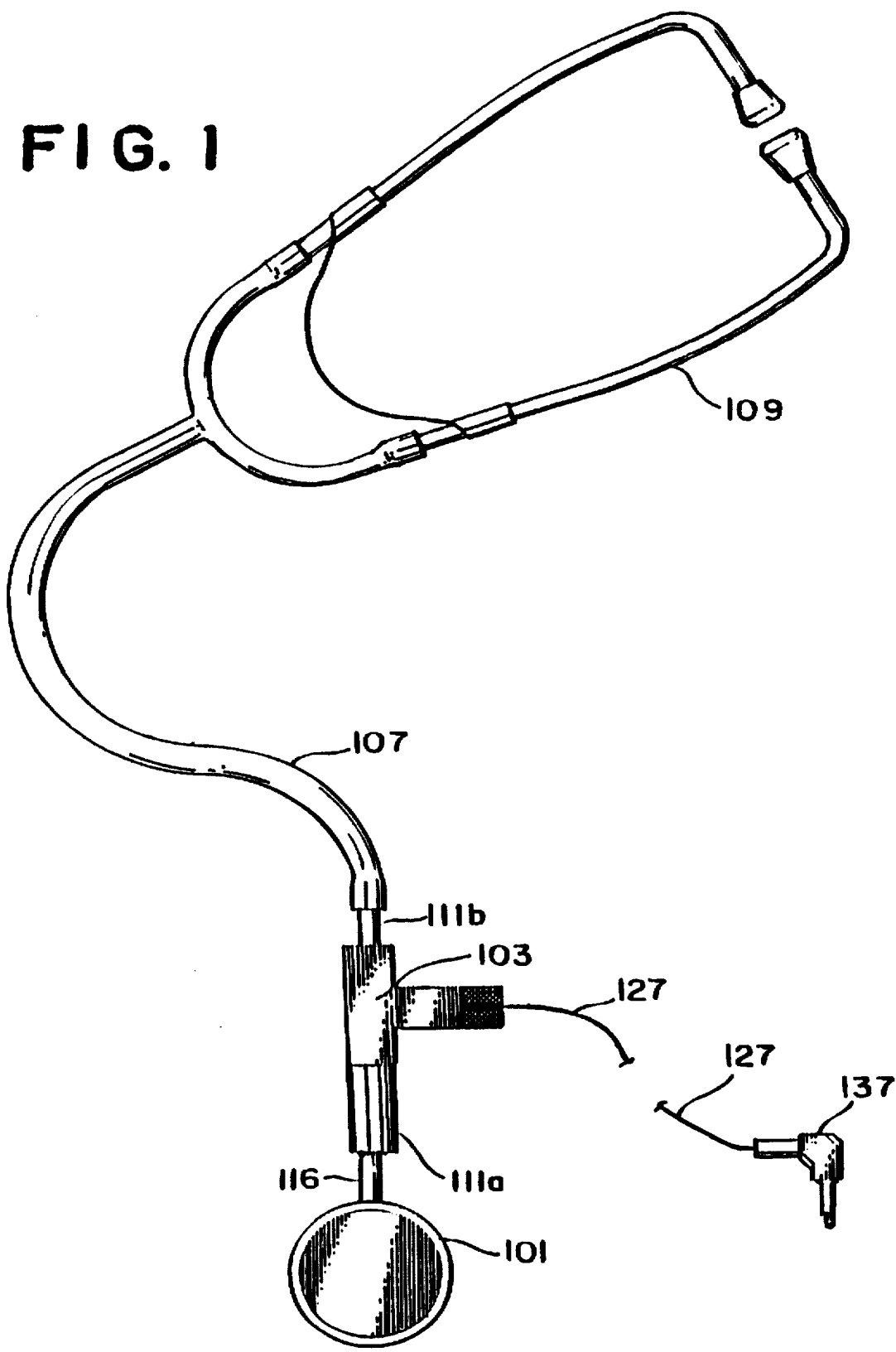
FIG. 1 shows a simplified cutaway view of an adapter according to a preferred embodiment of the present invention incorporated into a standard stethoscope.
Figure 2:
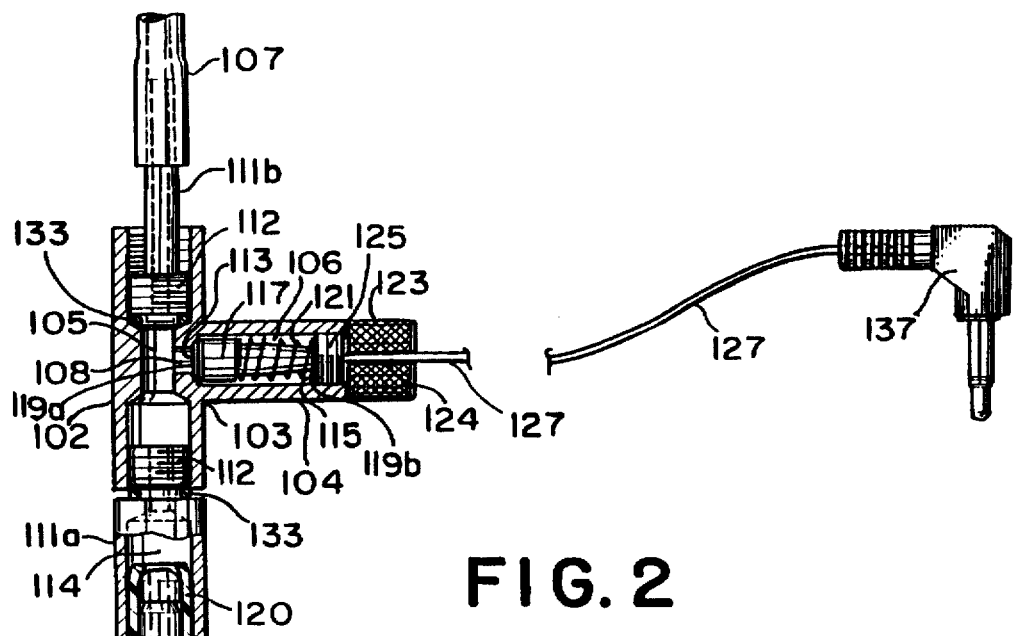
FIG. 2 shows a detailed cutaway view of an adapter according to a preferred embodiment of the present invention.
Figure 3:
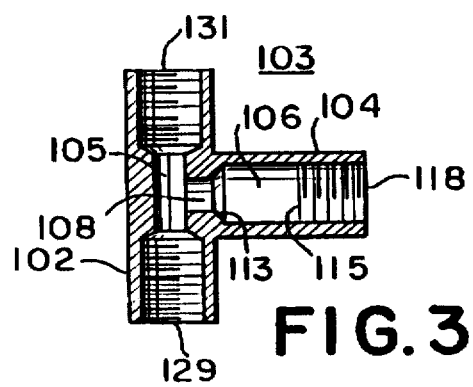
FIG. 3 shows a cutaway view of a housing of an adapter according to a preferred embodiment of the present invention.
Figure 7:
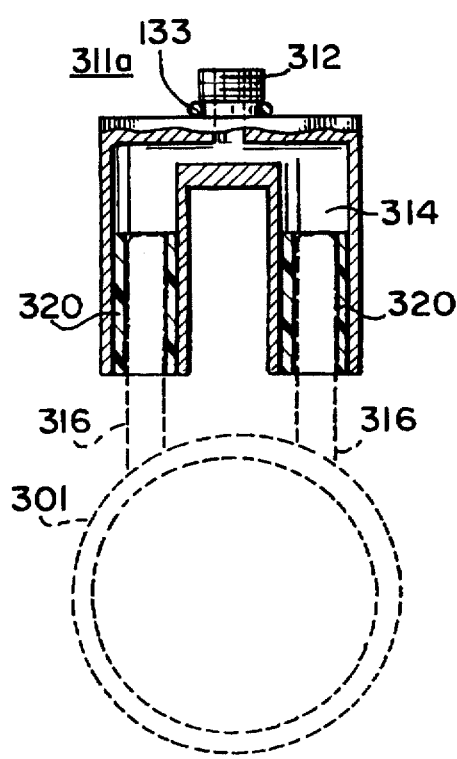
FIG. 7 shows a cutaway view of a bifurcated female coupler according to a preferred embodiment of the present invention.
Figure 10A:
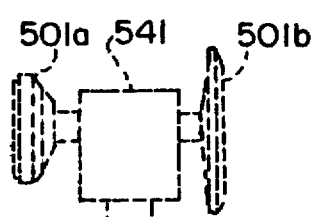
FIG. 10 shows a simplified plan view of the adapter of FIG. 9 incorporated into one type of standard stethoscope.

Standard stethoscopes come in several basic configurations. In one configuration the transducer 101 is a single molded piece having a single tube 116 extending therefrom (as shown in FIG. 1). This type of stethoscope is referred to as a monaural stethoscope as it has a single air column from the transducer to the earpiece where the column is divided. In another configuration, the transducer 301 has a pair of tubes 316 extending therefrom (as shown in FIG. 7). This type of stethoscope is referred to as a binaural or bifurcated stethoscope as it has two air columns extending from the transducer, one to each earpiece. In yet another basic configuration, instead of a single molded transducer, the stethoscope has a connector 541 to which one or more stethoscope transducers can be threaded (as shown in FIG. 10A) o Within these basic configurations, stethoscopes vary in the size of the hose and tubes employed.

Referring now to FIGS. 1-5, an adapter according to a preferred embodiment of the present invention comprises a housing 103 having a conduit 105 for conducting sound therethrough, a first coupler 111a for coupling the housing 103 to the transducer 101 of a standard stethoscope, a second coupler 111b for coupling the housing 103 to the sound conduction hose 107 of a standard stethoscope, and a transducer 117 for converting an audible tone to an electronic signal.

In a preferred embodiment of the present invention, the housing 103 is a branched member having a first branch 102 and second branch 104 perpendicular to the first branch 102. The first branch 102 is formed to define a conduit 105 therethrough terminating in a distal port 129 and proximal port 131. Both the distal port 129 and the proximal port 131 are preferably threaded to receive threaded couplers 111a and/or 111b. The second branch 104 is formed to define a chamber 106. The chamber 106 is in communication with the conduit 105 at one end of the chamber 106 through aperture 108. Aperture 108 is formed by annular shoulder 113. A first O-ring 119a rests against annular shoulder 113 inside chamber 106. Chamber 106 widens near the opposite end forming a second annular shoulder 115. A second O-ring 119b rests against annular shoulder 115. The second end 118 of chamber 106 is open and has female threads.

The housing 103 is preferably as compact as possible while being large enough to house the transducer 117 and to accommodate the couplers 111a and 111b. In a preferred embodiment, the first branch 102 has a substantially square cross-section and is approximately 1-2 inches long and approximately 0.25-0.75 inch wide. In a preferred embodiment, the first branch 102 is approximately 1.55 inches long and approximately 0.5 inch wide. The diameter of the conduit 105 is preferably approximately 0.625 inch. The second branch 104 is preferably positioned in the center of the first branch 102. The second branch 104 has a substantially square cross-section and is large enough to house the transducer 117. The second branch 104 is approximately 0.8 inch long and 0.5 inch wide. The housing 103 may be made of any hard, sound insulating material such stainless steel.

The transducer 117 is a standard microphone 117, such as the Tie-Pin Omni-Directional™ microphone manufactured by Radio Shack. Microphone 117 is housed within chamber 106. The microphone 117 is held in chamber 106 against O-ring 119a by a spring 121.

The second end of the chamber 106 is closed by a removable stopper 123. The stopper 123 prevents echoes and excludes outside sounds. The stopper 123 has a conduit 124 therethrough to allow for the passage of cable 127 from the microphone 117 to an external power supply (not shown), and/or digital or analog recording unit (not shown), or telephone line (not shown). The stopper 123 has a threaded annular sleeve 125 for insertion into chamber 106. When the stopper 123 is inserted into the second end of the chamber 106, the end of the sleeve 125 rests against O-ring 119b. The second end of the spring 121 rests against the stopper 123 thereby biasing the microphone 117 against the first O-ring 119a.

Figure 4:
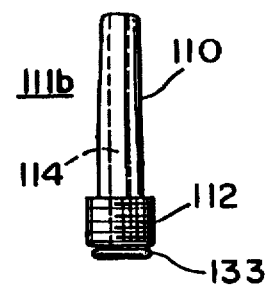
FIG. 4 shows a cutaway view of a male coupler according to a preferred embodiment of the present invention.
Figure 6:
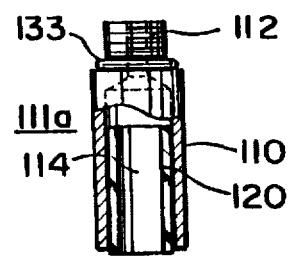
FIG. 6 shows a cutaway view of a female coupler according to a preferred embodiment of the present invention.

Adapter 100 has couplers 111a and 111b for coupling the transducer 101 of a standard stethoscope to the housing 103,
and for coupling the hose 107 of a standard stethoscope to the housing 103. The couplers 111 can be female or male as shown in FIGS. 6 and 4, respectively. Coupler 111a is female. Coupler 111b is male. Both male and female couplers 111 have a shaft 112, a receiving end 110, and a conduit 114 running through the entire length of the coupler 111 to permit the transmission of sound therethrough. As shown in FIG. 6, female coupler 111a has a straight receiving end 110. Receiving end 110 is lined with a compressible material 120, such as foam or rubber. Thus, in a preferred embodiment, a cylindrical piece of rubber 120 is fastened to the interior of the receiving end 110 of female fastener 111a.

Figure 8:
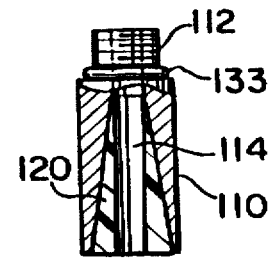
FIG. 8 shows a cutaway view of a female coupler according to an alternative embodiment of the present invention.

Since standard stethoscopes vary, the couplers 111a and 111b are formed to accommodate a variety of different size tubes 116 and hoses 107. Tubes 116 are generally male in that they are designed to be inserted into the hose 107 of a standard stethoscope. Thus, female coupler 111a will generally couple the tube 116 to the housing 103. To accomplish this, female coupler 111a has a straight receiving end 110 lined with a compressible material 120 to receive a variety of different size tubes 116. The smaller the diameter of the tube 116, the less the compressible material 120 will be compressed. In an alternative embodiment of the present invention, the female coupler has a tapered receiving end 110 as shown in FIG. 8.

The hose 107 of a standard stethoscope is generally female in that it is generally designed to receive tube 116. Thus, male coupler 111b will generally couple the hose 107 to the housing 103. Male coupler 111b has a wedge shaped receiving end to engage a variety of different size hoses 107. The greater the diameter of the hose 107, the farther the receiving end 110 of male coupler 111b is inserted into the hose 107.

The inner diameter of the receiving end 110 of female coupler 111a is sized to accommodate the vast majority of standard stethoscopes. The inner diameter of the receiving end 110 of the female coupler 111a is preferably approximately 0.25-0.75 inch. In a preferred embodiment of the present invention, the inner diameter of the receiving end 110 of the female coupler 111a is approximately 0.5 inch. In a preferred embodiment of the present invention, the compressible material 120 is approximately 0.125 inch thick. The outer diameter of the male coupler 111b is sized to accommodate the vast majority of standard stethoscopes. Thus, the outer diameter of the receiving end 110 of the male coupler 111b is preferably approximately 0.25-0.5 inch at the narrow end and approximately 0.375-0.625 inch at the wide end. In a preferred embodiment of the present invention, the outer diameter of the receiving end 110 of the male coupler 111b is approximately 0.375 inch at the wide end and approximately 0.25 inch at the narrow end.

The shafts 112 of the couplers 111a, 111b, 311a, and 311b are preferably threaded to thread into either the distal port 129 or the proximal port 131 of the housing 103. In a preferred embodiment, an O-ring 133 is disposed around the shaft 112 of the couplers 111a, 111b, 311a, and 311b.

Figure 5:
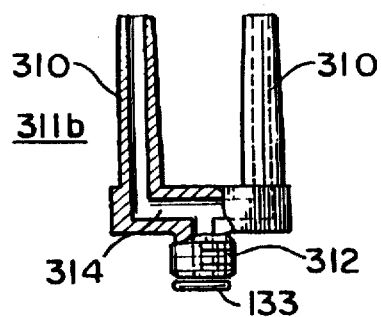
FIG. 5 shows a cutaway view of a bifurcated male coupler according to a preferred embodiment of the present invention.

Since some standard stethoscopes have bifurcated tubes (as shown in FIG. 7), the present invention also encompasses female and male bifurcated couplers 311a and 311b as shown in FIGS. 7 and 5, respectively. Bifurcated couplers 311a and 311b have a single shaft 312 and a bifurcated receiving end 310. As with couplers 111a and 111b, receiving ends 310 of bifurcated couplers 311a and 311b are adapted to fit the various sizes of standard bifurcated stethoscopes, and the shaft 312 is preferably threaded to thread into housing 103. Bifurcated couplers 311a and 311b also have conduits 314 running through both portions of the receiving end 310 and joining to run through shaft 312 to allow for transmission of sound therethrough.

Figure 9:
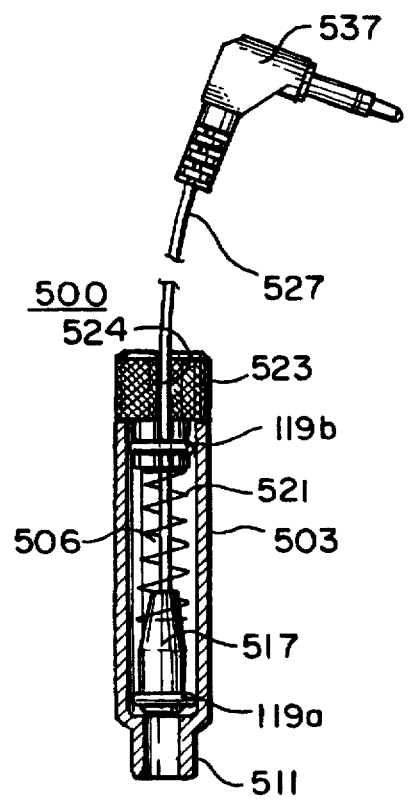
FIG. 9 shows a detailed cutaway view of an adapter according to an alternative preferred embodiment of the present invention.

An adapter 500 according to an alternative embodiment of the present invention is shown in FIG. 9. Adapter 500 differs from adapter 100 primarily in that adapter 500 has a straight housing 503 rather than a branched housing 103. Adapter 500 has port 511 which is adapted to receive couplers 111 or 311 (as shown in FIG. 11). Alternatively, adapter 511 may be threaded as shown in FIG. 9, for threading directly onto the stethoscope transducers of those stethoscopes having a metal connector to which one or more transducers 501a and/or 501b can be threaded (as shown in FIG. 10). Adapter 500 has a microphone 517 held in place by a spring 521 as in adapter 100. Adapter 500 also has a stopper 523 for preventing echoes and the admission of external sounds. The stopper 523 has a conduit 524 therethrough to allow for the passage of cable 527 from the microphone 117 to an external power supply (not shown), and/or digital or analog recording unit(not shown), or telephone line (not shown).

The housing 503 is also preferably as compact as possible while being large enough to house the microphone 117. In a preferred embodiment, the housing 503 has a substantially circular cross-section and is approximately 2 inches long and has an outer diameter of approximately 0.5 inch. The diameter of the chamber 506 is large enough to house the microphone 117. In a preferred embodiment the inner diameter of the chamber 506 is approximately 0.312 inch. The housing 503 may be made of any hard, sound insulating material, such as stainless steel. In a preferred embodiment, the housing 503 has a knurled exterior to facilitate gripping.

As can be seen from the above description, adapters according to the present invention can be used to reversibly convert the vast majority of standard stethoscopes. Thus, a medical professional can purchase a single adapter to reversibly convert whatever standard stethoscope he or she may own to a multimedia and/or telemedicine ready stethoscope. The medical professional can then use the converted stethoscope to listen to heart, lung, or other sounds, while simultaneously transmitting the sound to an electronic recording device. The electronic device may record, analyze, transmit, amplify, and/or replay the sound. Thus, medical professionals will be able to use the same simple, inexpensive stethoscope they have always used and are comfortable with while still keeping pace with the computerization revolution sweeping through the medical profession. The use of adapters according to the present invention with a variety of differently configured standard stethoscopes is discussed in more detail below.

Referring again to FIGS. 1–5, adapter 100 can be used with most standard stethoscopes as follows. (1) The transducer 101 of the standard stethoscope is detached from the hose 107. If the stethoscope is bifurcated (as shown in FIG. 7), both hoses are removed from the transducer. (2) Female coupler 111a is inserted into the distal port 129 of housing 103. If the stethoscope is bifurcated, female coupler 311a is inserted into distal port 129 of housing 103. (3) Tube 116 is inserted into receiving end 110 of coupler 111a. If the stethoscope is bifurcated, tubes 116 are inserted into receiving ends 310. (4) A male coupler 111b is inserted into the proximal port 131 of housing 103. If the stethoscope is bifurcated, a bifurcated male coupler 311b is inserted in the proximal port 131 of housing 103. (5) Receiving end 110, or ends 310, of the second coupler 111b, or 311b, are inserted into the hose(s) 107. (6) Jack 137 is connected to the desired recording or transmission unit. (7) The physician or other medical professional may then use the stethoscope in the usual manner, listening to sounds while simultaneously recording and/or transmitting the sounds electronically.

Referring now to FIG. 9, adapter 500 can be used with most standard stethoscopes as follows. (1) The transducer 101 of the standard stethoscope is detached from the hose 107. If the stethoscope is bifurcated (as shown in FIG. 7), both hoses are removed from the transducer. (2) Coupler 111, or 311, is inserted into the port 511 of housing 503. (3) Receiving end 110, or 310, is inserted into the tube(s) 116. (4) Jack 137 is connected to the desired recording or transmission unit. (5) Since a stethoscope converted according to this embodiment of the present invention will not permit the user to listen to the sounds directly, it is anticipated that a stethoscope converted in this manner would most likely be used for telemedicine. Thus, a medical professional, or even a patient, who is being directed remotely would place the transducer of the converted stethoscope on the appropriate portion of the patient's body. The sound would then be transmitted to the medical professional who will hear the sound remotely.

Figure 10B:
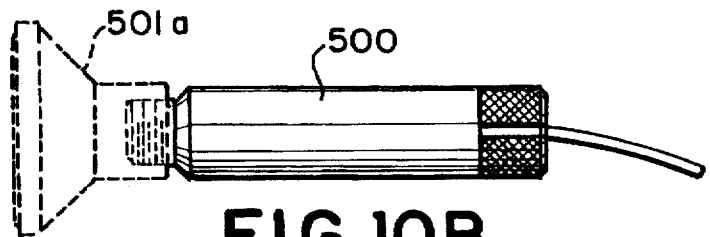
Figure 11:
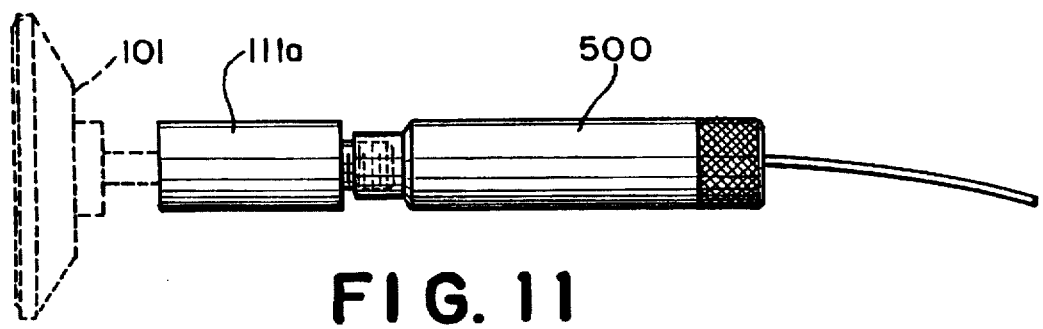
FIG. 11 shows a simplified plan view of the adapter of FIG. 9 incorporated into another type of standard stethoscope.

As stated above, some stethoscopes have a connector to which a plurality of transducers, such as a diaphragm and bell can be threaded, as shown in FIGS. 10A and 10B. Such a stethoscope can be converted as follows with an adapter 500 according to an alternative preferred embodiment of the present invention: (1) Either the bell 501a or diaphragm 501b is removed from the connector 541. (2) Adapter 500, having threaded port 511 is threaded onto the threads of the bell 501a or the diaphragm 501b. (3) Jack 537 is connected to the desired recording or transmission unit.

The present invention may be embodied in other specific forms without departing from the spirit or essential attributes of the invention. For example, an adapter according to the present invention can be configured with two male couplers 111b rather than both a female coupler 111a and a male coupler 111b. Where two male couplers 111b are used, the tube 116 is coupled to a small piece of hose which is in turn coupled to the male coupler 111b of the adapter housing 103.

It will be further understood that various other changes in the details, materials, and arrangements of the parts which have been described and illustrated in order to explain the nature of this invention may be made by those skilled in the art without departing from the principle and scope of the invention as expressed in the following claims.

What is claimed is:

1. An adapter for standard stethoscopes having a stethoscope transducer for picking up a sound signal connected to an earpiece for receiving the sound signal by a flexible hose for guiding the sound signal from the stethoscope transducer to the earpiece, said adapter being for reversibly converting standard stethoscopes to multimedia and telemedicine ready stethoscopes without significantly altering the look, feel, or performance of the standard stethoscopes comprising:

(a) a housing having means for conducting sound therethrough from the stethoscope transducer through the hose to the earpiece;

(b) means for coupling the housing to the stethoscope between the stethoscope transducer and the earpiece;

(c) a second transducer in the housing for converting a sound signal from the first said stethoscope transducer to an electronic signal without interfering with the conduction of the sound signal from the first transducer to the earpiece, and wherein the coupling means is adapted to reversibly couple the housing to the first transducer and the hose leading to the earpiece of a standard stethoscopes, wherein:

the housing is a branched member having a first branch and a second branch;

the first branch is formed to define a conduit therethrough between said first transducer and the earpiece;

the second branch is formed to define a chamber; and the chamber is in communication with the conduit.

wherein the means for coupling the housing to the stethoscope comprises:

means for directly and physically coupling the housing to the stethoscope transducer; and means for directly and structurally coupling the housing to the hose leading to the earpiece.

the means for coupling the housing to the stethoscope transducer is a first coupler; and the means for coupling the housing to the hose is a second coupler, wherein the first coupler is a female coupler and the second coupler is a male coupler, wherein:

the female coupler has a receiving end and a conduit therethrough; and the conduit is lined with compressible material.

2. The adapter of claim 1, wherein at least one of the couplers is a bifurcated coupler.

3. The adapter of claim 1, wherein the couplers are removably coupled to the housing.

4. The adapter of claim 2, wherein the couplers are removably coupled to the housing.

5. The adapter of claim 1, wherein the second transducer is housed in the chamber.

6. The adapter of claim 1, wherein the second transducer is a microphone capable of generating an electronic signal compatible with standard analog and digital recording devices.

7. The adapter of claim 6, wherein the microphone is capable of generating an RF-11 signal.

8. The adapter of claim 1 wherein:

the female coupler has a receiving end and a conduit therethrough;

the conduit is lined with a compressible material;

the couplers are removably coupled to the housing;

the second transducer is housed in the chamber;

the second transducer is a microphone capable of generating an electronic signal compatible with standard analog and digital recording devices; and the microphone is capable of generating an RF-11 signal.

* * * * *